United States Patent
Ho et al.

(10) Patent No.: US 10,383,528 B2
(45) Date of Patent: Aug. 20, 2019

(54) WEARABLE APPARATUS AND PHOTOPLENTHYSMOGRAPHY SENSOR UNIT THEREOF

(71) Applicants: LITE-ON OPTO TECHNOLOGY (CHANGZHOU) CO., LTD., Changzhou, Jiangsu (CN); LITE-ON TECHNOLOGY CORPORATION, Taipei (TW)

(72) Inventors: Tsan-Yu Ho, New Taipei (TW); Meng-Sung Chou, New Taipei (TW); Ming-Kun Weng, New Taipei (TW); Chiou-Yueh Wang, New Taipei (TW); Fang-Yi Chang, New Taipei (TW); Ren-Guey Lee, New Taipei (TW); Hui-Chia Kuo, New Taipei (TW)

(73) Assignees: LITE-ON OPTO TECHNOLOGY (CHANGZHOU) CO., LTD., Changzhou, Jiangsu Province (CN); LITE-ON TECHNOLOGY CORPORATION, Taipei (TW)

( * ) Notice: Subject to any disclaimer, the term of this patent is extended or adjusted under 35 U.S.C. 154(b) by 241 days.

(21) Appl. No.: 15/411,937

(22) Filed: Jan. 20, 2017

(65) Prior Publication Data
US 2017/0224236 A1  Aug. 10, 2017

(30) Foreign Application Priority Data
Feb. 5, 2016  (CN) .......................... 2016 1 0083054

(51) Int. Cl.
*A61B 5/021*  (2006.01)
*A61B 5/0404*  (2006.01)
(Continued)

(52) U.S. Cl.
CPC ........ *A61B 5/02108* (2013.01); *A61B 5/0205* (2013.01); *A61B 5/0261* (2013.01);
(Continued)

(58) Field of Classification Search
CPC .............. A61B 5/02108; A61B 5/0261; A61B 5/02125; A61B 5/681; A61B 5/7278;
(Continued)

(56) References Cited

U.S. PATENT DOCUMENTS

| | | | |
|---|---|---|---|
| 2015/0265214 A1* | 9/2015 | De Kok | A61B 5/6843 600/301 |
| 2016/0029911 A1* | 2/2016 | Lee | A61B 5/02427 600/301 |
| 2017/0209053 A1* | 7/2017 | Pantelopoulos | A61B 5/02125 |

* cited by examiner

*Primary Examiner* — Mark Bockelman
(74) *Attorney, Agent, or Firm* — Li & Cai Intellectual Property (USA) Office

(57) ABSTRACT

A wearable apparatus and a photoplethysmograph (PPG) sensor unit are provided. The wearable apparatus includes a wearable holder and a physiological information measurement module configured to the wearable holder. The physiological information measurement module includes a circuit board, an electrocardiograph (ECG) sensor unit and a PPG sensor unit. The PPG sensor unit is disposed on the circuit board and adapted to be used in conjunction with the ECG sensor unit electrically connected to a first pad and a second pad on the circuit board. The PPG sensor unit includes a grid having a plurality of accommodating spaces, a lighting element arranged in one of the accommodating spaces, and a photo sensor arranged in another accommodating space. The grid includes an inner conductive contact portion exposed from the wearable holder, facing an inner side of the wearable holder and electrically connected to the second pad.

21 Claims, 11 Drawing Sheets

(51) Int. Cl.
*A61B 5/00* (2006.01)
*A61B 5/0205* (2006.01)
*A61B 5/024* (2006.01)
*A61B 5/026* (2006.01)
*A61B 5/0245* (2006.01)

(52) U.S. Cl.
CPC ...... *A61B 5/02125* (2013.01); *A61B 5/02427* (2013.01); *A61B 5/02438* (2013.01); *A61B 5/0404* (2013.01); *A61B 5/681* (2013.01); *A61B 5/7278* (2013.01); *A61B 5/742* (2013.01); *A61B 5/0245* (2013.01); *A61B 2562/0238* (2013.01)

(58) Field of Classification Search
CPC .............. A61B 5/0205; A61B 5/02427; A61B 5/02438; A61B 5/742; A61B 5/0404; A61B 2562/0238; A61B 5/0245
See application file for complete search history.

WEARABLE APPARATUS AND PHOTOPLENTHYSMOGRAPHY SENSOR UNIT THEREOF

BACKGROUND OF THE INVENTION

1. Field of the Invention

The instant disclosure relates to a wearable measuring apparatus and a photoplethysmograph sensor unit thereof; in particular, to a blood-pressure measuring apparatus which is wearable around a user's wrist and a photoplethysmograph sensor unit thereof.

2. Description of Related Art

Most current wearable apparatus measures the rhythm of heart by using a photoplethysmograph sensor and measures the electrocardiography (ECG) signal by using an ECG sensor. However, providing a wearable apparatus with smaller size and lighter weight capable of measuring blood pressure for the convenience of users, especially elderly people, is another current development topic.

SUMMARY OF THE INVENTION

In order to achieve the aforementioned objects, according to an embodiment of the instant disclosure, a photoplethysmograph (PPG) sensor unit adapted to be implemented in a wearable apparatus and having a conductive grid is provided, in which the conductive grid can serve as one of the signal input electrodes for receiving the electrocardiography (ECG) signal so as to minimize the space occupation of the PPG sensor unit and the ECG sensor unit, and minimize the size and weight of the wearable blood-pressure measuring apparatus.

In order to further the understanding regarding the instant disclosure, the following embodiments are provided along with illustrations to facilitate the disclosure of the instant disclosure.

DETAILED DESCRIPTION OF THE PREFERRED EMBODIMENTS

The aforementioned illustrations and following detailed descriptions are exemplary for the purpose of further explaining the scope of the instant disclosure. Other objectives and advantages related to the instant disclosure will be illustrated in the subsequent descriptions and appended drawings.

Figure 1:
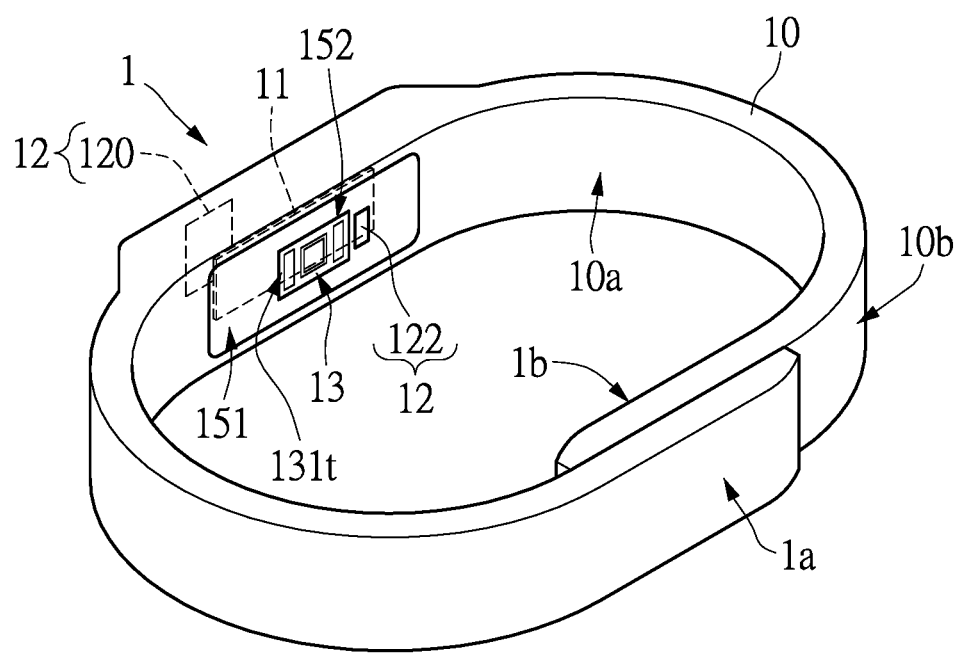
FIG. 1 shows a perspective view of a wearable apparatus according to an embodiment of the instant disclosure.
Figure 1A:
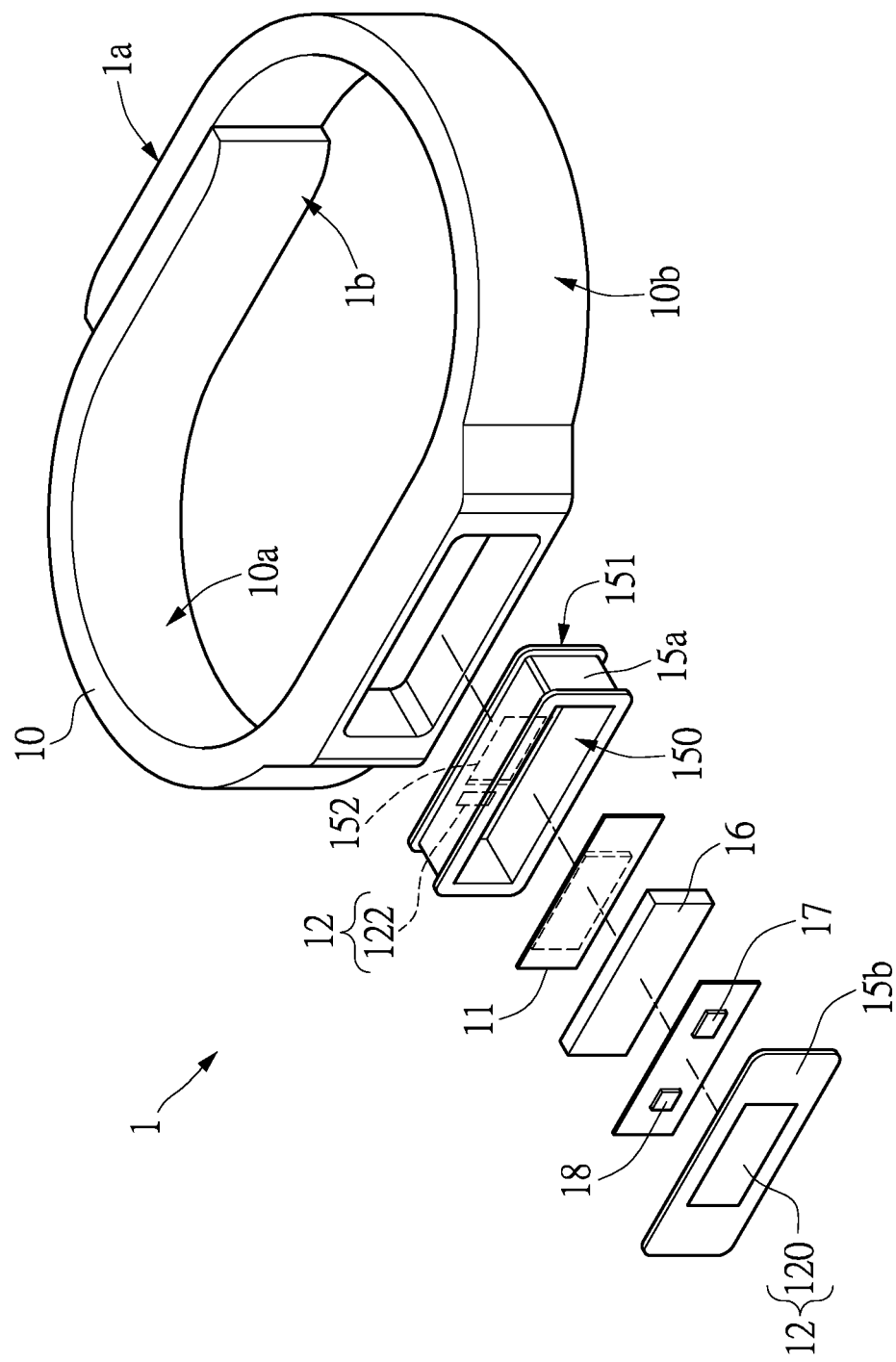
FIG. 1A shows an exploded schematic view of a wearable apparatus according to an embodiment of the instant disclosure.

Please refer to FIG. 1 and FIG. 1A. FIGS. 1 and 1A respectively show a perspective view and an exploded schematic view of a wearable apparatus according to an embodiment of the instant disclosure.

The wearable apparatus 1 includes a wearable holder 10, a physiological information measurement module 11, battery module 16, a power management module 17, and a communication module 18.

The wearable holder 10 is adapted to be worn on the user. For example, the wearable holder 10 is wearable around the user's wrist. Specifically, as shown in FIG. 1, the wearable holder 10 of the instant embodiment can have a similar shape to that of a watchband and the wearable holder 10 has two opposite ending portions 1a, 1b.

As shown in FIG. 1, the wearable holder 10 has an inner surface 10a and an outer surface 10b. When the user is wearing the wearable holder 10 on the hand, the inner surface 10a is closer to the user's skin.

The two opposite ending portions 1a, 1b of the wearable holder 10 can be joined together in a detachable way so that the wearable holder 10 can be held on the user's wrist or body. In one embodiment, the wearable holder 10 includes a male fastener and a female fastener respectively disposed on the two opposite ending portions 1a, 1b. The male fastener and the female fastener can be mated with each other when the two ending portions 1a, 1b are overlapped with each other. In another embodiment, the two ending portions 1a, 1b can be detachably jointed together through two magnetic members. Accordingly, the holding means of the wearable holder 10 on the user is not limited.

The physiological information measurement module 11, the battery module 16, the power management module 17, and the communication module 18 can be positioned at any position of the wearable holder 10. In the embodiment shown in FIG. 1, the physiological information measurement module 11, the battery module 16, the power management module 17 and the communication module 18 are positioned between two opposite ending portions 1a, 1b.

Specifically, referring to FIG. 1A, the wearable apparatus 1 further includes a housing 15a detachably disposed on the wearable holder 10 and a cover 15b disposed on the housing 15a. The cover 15b and the housing 15a commonly define an arrangement space 150 to accommodate the physiological information measurement module 11, the battery module 16, the power management module 17, and the communication module 18. In another embodiment, the housing 15a and the wearable holder 10 can be integrated into one-piece.

In the embodiments shown in FIG. 1 and FIG. 1A, the housing 15a has a bottom surface 151 and an opening 152 formed on the bottom surface 151. When the physiological information measurement module 11, the battery module 16, the power management module 17, and the communication module 18 are accommodated in the arrangement space 150, and the housing 15a is engaged with the wearable holder 10, the physiological information measurement module 11 can be partially exposed from the wearable holder 10 at an inner side of the wearable holder 10.

The electrical connections among the physiological information measurement module 11, the battery module 16, the power management module 17, and the communication module 18 are established. The battery module 16, such as a lithium battery, can supply power to the physiological information measurement module 11. The power management module 17 for managing power consumption of the battery module 16 and the communication module 18 can be integrated on the same printed circuit board. The communication module 18 can transfer the data obtained by the physiological information measurement module 11 to the cloud or the other electronic devices. The communication module 18 is such as a Bluetooth communication system.

Figure 2A:
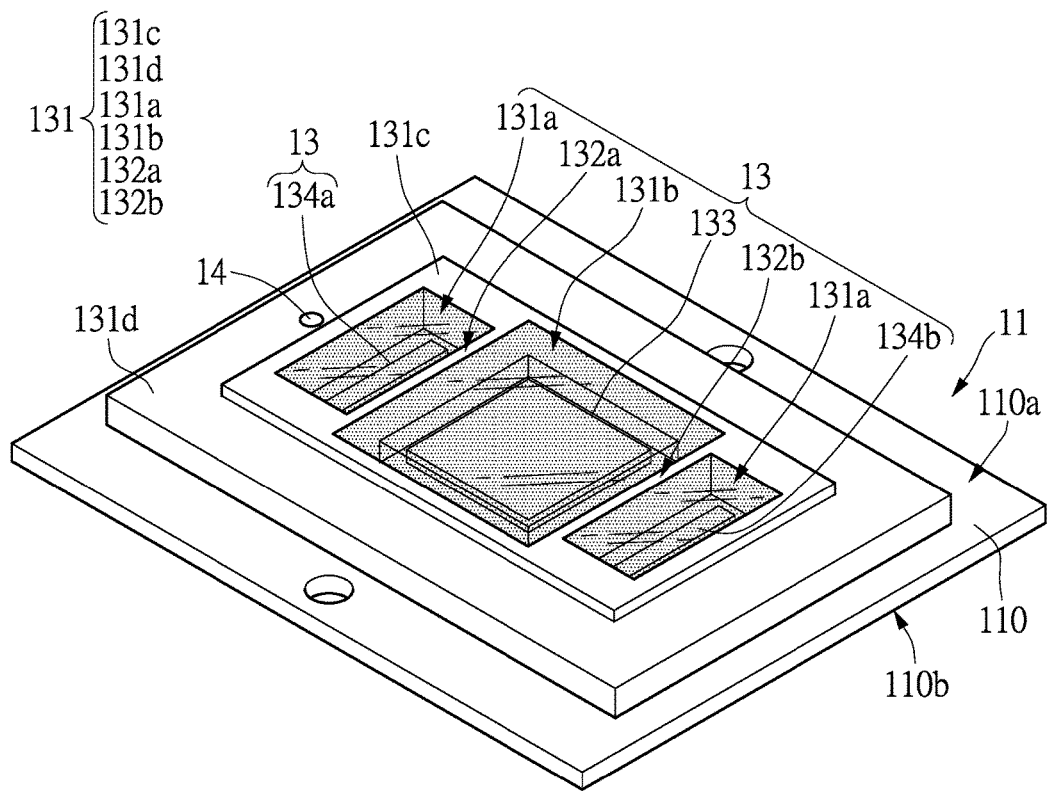
FIG. 2A shows a perspective view of a physiological information measurement module according to an embodiment of the instant disclosure.
Figure 2B:
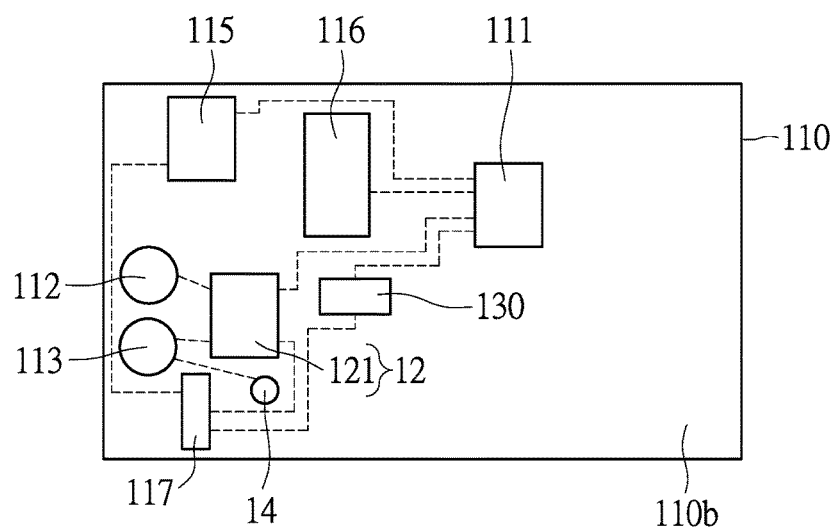
FIG. 2B shows a bottom view of the physiological information measurement module according to an embodiment of the instant disclosure.

Please refer to FIG. 1, FIG. 2A, and FIG. 2B. FIG. 2A shows a perspective view of a physiological information measurement module according to an embodiment of the instant disclosure, and FIG. 2B shows a bottom view of the physiological information measurement module according to an embodiment of the instant disclosure. The physiological information measurement module 11 includes a circuit board 110, an electrocardiograph (ECG) sensor unit 12, and a photoplethysmograph (PPG) sensor unit 13.

As shown in FIG. 1, the PPG sensor unit 13 of the physiological information measurement module 11 is exposed at the inner side of the wearable holder 10 through the opening 152 of the housing 15a to be in contact with the user's skin. In the instant disclosure, the portion of the PPG sensor unit 13 exposed from the opening 152 is defined as an inner conductive contact portion 131t. Notably, the inner conductive contact portion 131t can be completely made of conductive material or a portion of the inner conductive contact portion 131t can be made of conductive material. The details and the structure of the PPG sensor unit 13 will be described following.

Please refer to FIG. 2A. The circuit board 110 has a front surface 110a and a rear surface 110b. In the instant embodiment, the circuit board 110 includes a plurality of traces, pads and functional chips configured thereon, in which the electrical connections among the pads and the functional chips are established through the traces.

Please refer to FIG. 2B. Only some of the traces, pads and functional chips are illustrated in FIG. 2B. However, one of ordinary skill in the art should understand that the numbers and the arrangements of the traces, the pads and the functional chips of the circuit board 110 can be designed based on practical demand. Thus, the embodiment shown in FIG. 2B is not intended to limit the scope of the instant disclosure. In the instant embodiment, at least a signal processing unit 111, a first pad 112, and a second pad 113 are disposed on the rear surface 110b of the circuit board 110.

Please refer to FIG. 1A and FIG. 2B. The ECG sensor unit 12 includes an electrocardiograph (ECG) sensing control chip 121 and an outer conductive contact portion 120. The ECG sensing control chip 121 is disposed on the rear surface 110b of the circuit board 110 and electrically connected to the first pad 112 and the second pad 113. The outer conductive contact portion 120 is exposed outwardly and electrically connected to the first pad 112. As shown in FIG. 1A, the outer conductive contact portion 120 is located at a top surface of the cover 15b and exposed at an outer surface 10b of the wearable holder 10. Notably, the electrical connection between the outer conductive contact portion 120 and the first pad 112 can be established by any well-known means, description of which is omitted herein.

Please refer to FIG. 2B. The ECG sensing control chip 121 is electrically connected to the signal processing unit 111, the first pad 112, and the second pad 113. Specifically, the ECG sensing control chip 121 has two signal input terminals respectively electrically connected to the first pad 112 and the second pad 113 so as to receive the ECG signals. The ECG sensing control chip 121 converts the received ECG signals to digital signals. The signal processing unit 111 analyzes and processes the received digital signals.

Please refer to FIG. 1. The outer conductive contact portion 120 of the ECG sensor unit 12 is exposed at the outer side of the wearable holder 10 to serve as one of the signal input electrodes of the ECG sensor unit 12. It is convenient for the user to touch the outer conductive contact portion 120. The outer conductive contact portion 120 of the instant embodiment is disposed on the top surface of the cover 15b, but in another embodiment, the outer conductive contact portion 120 can be positioned at an outer surface 10b of the wearable holder 10. As long as it is convenient for the user to directly touch the outer conductive contact portion 120 so that the ECG sensor unit 12 can measure the ECG signal, the position of the outer conductive contact portion 120 is not limited herein.

Additionally, in the embodiment of the instant disclosure, the second pad 113 is electrically connected to the inner conductive contact portion 131t of the PPG sensor unit 13, which is exposed from the opening 152 of the housing 15a. That is, the inner conductive contact portion 131t of the PPG sensor unit 13 can be directly touched by the user and serve as another signal input electrode of the ECG sensor unit 12. The functions and the structures of the PPG sensor unit 13 and the inner conductive contact portion 131t will be described in detail below.

Furthermore, in the embodiment shown in FIG. 1 and FIG. 1A, the ECG sensor unit 12 can further include a ground electrode 122 disposed at the inner side of the wearable holder 10. As shown in FIG. 1A, the ground electrode 122 is disposed on the bottom surface 151 of the housing 15a. By the arrangement of the ground electrode 122, the noise generated during receiving the ECG signals can be attenuated to improve the accuracy of the ECG signals. In another embodiment, the ground electrode 122 also can be disposed on the inner surface 10a of the wearable holder 10 or omitted.

Please refer to FIG. 2A and FIG. 2B. The PPG sensor unit 13 of the instant embodiment for measuring photoplethysmograph (PPG) signals includes a photo sensing control chip 130 disposed on the rear surface 110b of the circuit board 110, and a grid 131, a first lighting element 134a, a second lighting element 134b and a photo sensor 133, which are disposed on the front surface 110a of the circuit board 110.

The photo sensing control chip 130 can be electrically connected to the first lighting element 134a, the second lighting element 134b and the photo sensor 133 through the traces (not shown in FIG. 2A and FIG. 2B) embedded in the circuit board 110. The photo sensing control chip 130 can control the on/off states of the first and second lighting elements 134a, 134b and receive the signals detected by the photo sensor 133.

Furthermore, the photo sensing control chip 130 electrically connected to the signal processing unit 111 transmits the detected PPG signals to the signal processing unit 111 and then the signal processing unit 111 converts the PPG signals to digital signals.

The signal processing unit 111 can include one or more processors, controllers, microprocessors, microcontrollers, application-specific integrated circuits, digital signal processors, programmable logic devices (PLD), field programmable gate arrays (FPGA) and memory or any combination thereof. The signal processing unit 111 can record data and provide commands to each of the passive components. The signal processing unit 111 can receive, calculate, and analyze the signals detected by each of the sensing elements, and then output the results.

Please refer to FIG. 2A. Both of the first lighting element 134a and the second lighting element 134b can be light emitting diodes (LEDs). The first and second lighting elements 134a, 134b can respectively generate different detecting lights with different wavelengths for projecting on an object to be tested of (e.g., one of the user's wrists). In one embodiment, the wavelength of the detecting light generated by the first lighting element 134a ranges from 510 nm to 550 nm, the wavelength of the detecting light generated by the second lighting element 134b ranges from 550 nm to 600 nm.

Accordingly, for the user having normal skin color, the PPG signals can be obtained by the detecting light with shorter wavelength generated by the first lighting element 134a. In addition, for the user having dark skin color or a tattoo, the PPG signals can be obtained by the detecting light with longer wavelength generated by the second lighting element 134b. As such, more accurate PPG signals can be obtained by the photo sensor 133.

In another embodiment, the detecting light generated by the first lighting element 134a can have the same wavelength (for example, about 510 nm to 550 nm) as that of the other detecting light generated by the second lighting element 134b. In another embodiment, the second lighting element 134b can be omitted, and only the first lighting element 134a is used for providing the detecting light.

The photo sensor 133, such as a photodiode, can be used to receive the reflected light reflected by a tested object and record the variations of the reflected light to obtain the PPG signals.

Please refer to FIG. 2A. The grid positioned at the front surface 110a of the circuit board 110 can be divided into an inner surrounding portion 131c, an outer surrounding portion 131d, a first partition portion 132a, and a second partition portion 132b. The inner surrounding portion 131c surrounds the first lighting element 134a, the second lighting element 134b, and the photo sensor 133, and the outer surrounding portion 131d surrounds the inner surrounding portion 131c. The inner surrounding portion 131c, the first partition portion 132a, and the second partition portion 132b commonly defines a plurality of accommodating spaces 131a, 131b. In the instant embodiment, the photo sensor 133 is located in the central accommodating space 131b. The first lighting element 134a and the second lighting element 134b are respectively located in two accommodating spaces 131a which are located at two opposite sides of the photo sensor 133. That is, the first partition portion 132a separates the first lighting element 134a from the photo sensor 133, and the second partition portion 132b separates the second lighting element 134b from the photo sensor 133.

Notably, because the photo sensor 133 is arranged between the first and second lighting elements 134a, 134b, the interference of the ambient light with the PPG signals detected by the photo sensor 133 can be minimized to improve the accuracy of the PPG signals. Additionally, the first partition portion 132a and the second partition portion 132b can block the detecting light generated by the first lighting element 134a and the second lighting element 134b from entering the photo sensor 133 directly, thereby attenuating the interference of the detecting light with the PPG signals obtained by the photo sensor 133.

Figure 3A:
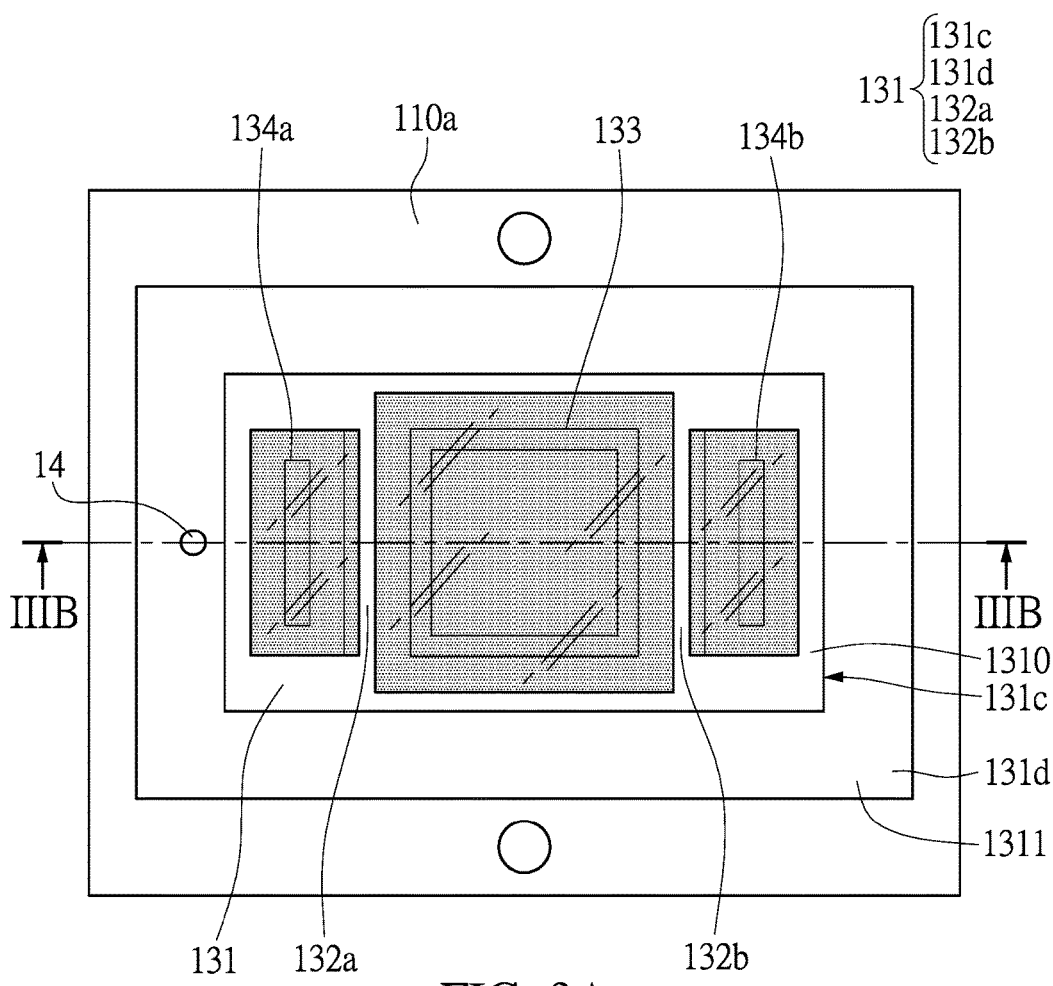
FIG. 3A shows a top view of the physiological information measurement module according to an embodiment of the instant disclosure.
Figure 3B:
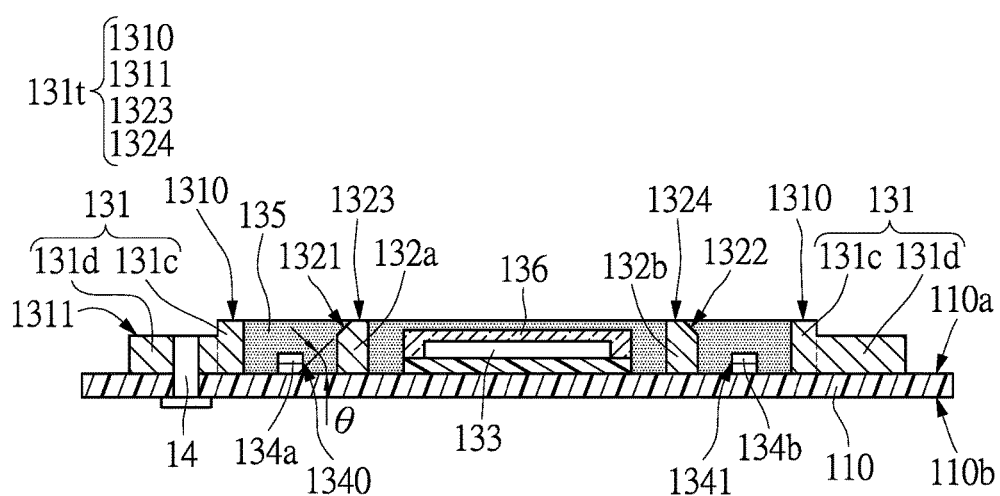
FIG. 3B shows a cross-sectional view taken along line IIIB-IIIB in FIG. 3A.

Please refer to FIG. 3A and FIG. 3B. FIG. 3A shows a top view of the physiological information measurement module according to an embodiment of the instant disclosure; and FIG. 3B shows a cross-sectional view taken along line IIIB-IIIB in FIG. 3A.

As shown in FIG. 3B, the detailed structures of the first partition portion 132a and the second partition portion 132b are illustrated. In the instant embodiment, the first partition portion 132a includes a first inclined light-guiding surface 1321 for guiding the detecting light generated by the first lighting element 134a accumulating and projecting on the object to be tested, so that the photo sensor 133 can obtain more accurate PPG signals. The first inclined light-guiding surface 1321 is formed at the top portion of the first partition portion 132a and adjacent to the first lighting element 134a. The first inclined light-guiding surface 1321 is inclined along a direction from a top surface 1323 of the first partition portion 132a to the first lighting element 134a. The first inclined light-guiding surface 1321 is inclined with respect to the front surface 110a of the circuit board 110 by an angle ranging from 10 to 80 degrees. That is, the first inclined light-guiding surface 1321 and a horizontal reference plane form an angle ranging from 10 to 80 degrees. In one preferred embodiment, the angle formed between the first inclined light-guiding surface 1321 and the horizontal reference plane ranges from 25 to 65 degrees due to the size limitation.

Similarly, the second partition portion 132b includes a second inclined light-guiding surface 1322 formed at the top portion thereof and adjacent to the second lighting element 134b. The second inclined light-guiding surface 1322 is inclined along another direction from a top surface 1324 of the second guiding surface 1322 to the second lighting element 134b. Specifically, the second inclined light-guiding surface 1322 is inclined with respect to the front surface 110a of the circuit board 110 and forms an angle ranging from 10 to 80 degrees. That is, the second inclined light-guiding surface 1322 and a horizontal reference plane form an angle ranging from 10 to 80 degrees. In one preferred embodiment, the angle formed between the second inclined light-guiding surface 1322 and the horizontal reference plane ranges from 25 to 65 degrees.

Specifically, the inclined angles of the first and second inclined light-guiding surfaces 1321, 1322 can be adjusted according to the sizes, the thicknesses of the first lighting element 134a and the second lighting element 134b, and the relative positions of the first lighting element 134a and the second lighting element 134b in the accommodating spaces 131a.

The first lighting element 134a includes a side surface 1340 facing to the first partition portion 132a. In one preferred embodiment, an extending direction of the first inclined light-guiding surface 1321 passes through the side surface 1340 of the first lighting element 134a. Similarly, the second lighting element 134b includes a side surface 1341 facing to the second partition portion 132b, and an extending direction of the second inclined light-guiding surface 1322 passes through the side surface 1341 of the second lighting element 134b.

Through the design of the inclined angles of the first and second inclined light-guiding surfaces 1321, 1322, the direction in which the detecting light generated by the first lighting element 134a and the second lighting element 134b is transmitted can be controlled. The detecting light can be projected directly and accurately to the object to be tested (e.g., one of the user's wrists) and then reflected and transmitted to the photo sensor 133, and then the photo sensor 133 receives the light reflected by the objected to be tested and records the variations of the reflected light based on which the PPG signals is calculated.

When the detecting lights produced by the first lighting element 134a and the second lighting element 134b are monochromatic, the first and second inclined light-guiding surfaces 1321, 1322 are substantially symmetrical with each other and inclined with respect to the horizontal reference plane by substantially the same angle.

Additionally, in the instant embodiment, the grid 131 is completely made of conductive materials, and can also be called a conductive grid. The grid 131 is electrically connected to the second pad 113, which is arranged on the circuit board 110 and electrically connected to the ECG control sensing chip 121. Accordingly, the grid 131 not only prevents the photo sensor 133 from interference by the detecting lights produced by the first and second lighting elements 134a, 134b, but also is adapted to be touched by the user to serve as one of the signal input electrodes of the ECG sensor unit 12.

As mentioned above, referring to FIG. 1, the grid 131 includes the inner conductive contact portion 131t exposed inwardly and disposed opposite to the outer conductive contact portion 120. Specifically, in one embodiment, the inner conductive contact portion 131t is exposed from the wearable holder 10 with the inner conductive contact portion 131t facing an inner side of the wearable holder 10. In the instant embodiment, the inner conductive contact portion 131t is exposed at the inner surface 10a and adapted to be touched by the user.

In one embodiment, the inner conductive contact portion 131t includes the top surface 1310 of the inner surrounding portion 131c, the top surface 1311 of the outer surrounding portion 131d, the top surface 1323 of the first partition portion 132a, and the top surface 1324 of the second partition portion 132b. That is, the top surface 1310 of the inner surrounding portion 131c, the top surface 1311 of the outer surrounding portion 131d, the top surface 1323 of the first partition portion 132a, and the top surface 1324 of the second partition portion 132b are exposed from the wearable holder 10 through the opening 152.

In another embodiment, the inner conductive contact portion 131t can only include the top surface 1310 of the inner surrounding portion 131c, the top surface 1323 of the first partition portion 132a, and the top surface 1324 of the second partition portion 132b. In other words, the area, shape, and position of the inner conductive contact portion 131t are not limited in the instant disclosure. When the user wears the wearable apparatus on the left hand and presses the outer conductive contact portion 120 with right hand, the inner conductive contact portion 131t can be directly in contact with the user's left hand, and the outer conductive contact portion 120 can be directly in contact with the user's right hand. As such, the ECG signals can be measured by the ECG sensor unit 12.

The PPG sensor unit 13 can measure the PPG signals simultaneously. Subsequently, the ECG signals and the PPG signals can be transmitted to the signal processing unit 111 to calculate the blood pressure.

Furthermore, in the instant embodiment, the inner conductive contact portion 131t includes a rough contact surface on which a surface treatment is performed so as to increase the contacting area with the human body, thereby decreasing the noise of the ECG signal. The surface treatment, such as blasting process or roughening process, for increasing the surface roughness of the inner conductive contact portion 131t can be performed in many ways and is not limited herein.

Because the grid 131 and the second pad 113 are respectively arranged at two opposite sides of the circuit board 110, the inner conductive contact portion 131t of the grid 131 is electrically connected to the second pad 113 through a conductive post 14.

Please refer to FIG. 3B. The conductive post 14 passes through the circuit board 110 to be electrically in contact with the grid 131. Referring to FIG. 2B, a portion of the conductive post 14 located at the rear surface 110b of the circuit board 110 can be electrically connected to the second pad 113 through a trace (not labeled). That is, the grid 131 is electrically connected to the second pad 113 through the conductive post 14 and the trace formed on the circuit board 110. In the instant embodiment, the conductive post 14 can be a fastening element made of conductive material.

However, other means for establishing the electrical connection between the grid 131 and the second pad 113 can be carried out and so this does not limit the scope of the instant disclosure. In another embodiment, by forming a contact between the grid 131 and a pad arranged at the front surface 110a and the traces embedded in the circuit board 110, the electrical connections between the grid 131 and the second pad 113 arranged on the rear surface 110b can be established. Furthermore, because the grid 131 is completely made of conductive material, the conductive post 14 can be selectively positioned in the outer surrounding portion 131d or in the inner surrounding portion 131c.

Please refer to FIG. 3B. The PPG sensor unit 13 further includes a protection layer 135 and a filter layer 136. The protection layer 135 covers and protects the first lighting element 134a, the second lighting element 134b, and the photo sensor 133 from damage due to moisture. Furthermore, the protection layer 135 can be made of material transparent to the detecting lights. The filter layer 136 is disposed on the photo sensor 133 for filtering the ultraviolet light and the ambient light with wavelength greater than 600 nm, thereby improving the accuracy of the measured signals.

Please refer to FIG. 2B. In the instant embodiment, the physiological information measurement module 11 further includes a gravity sensor 115, an oscillator 116, and a power convertor 117, which are electrically connected to the signal processing unit 111.

As shown in FIG. 2B, the gravity sensor 115, the oscillator 116, and the power convertor 117 are disposed on the rear surface 110b of the circuit board 110 and electrically connected to the signal processing unit 111, the ECG sensing control chip 121, and the photo sensing control chip 130 through the traces embedded in the circuit board 110.

The gravity sensor 115 can detect the inclined angle of the physiological information measurement module 11 with respect to a horizontal plane to obtain a movement signal, and transmits the movement signal to the signal processing unit 111. When the user wears the wearable apparatus 1, movement, walking, or posture changes can be detected by the gravity sensor 115. The signal processing unit 111 can eliminate noise according to the movement signals during the collection of dynamic information, and the signal processing unit 111 can provide the state information related to the step-counts measurement, sleep state, tired state, or emotional state to the user.

The oscillator 116, such as a crystal oscillator, can be used to form a clock stabilization circuit. In the embodiment of the instant disclosure, the signal processing unit 111 can control the ECG sensor unit 12 and the PPG sensor unit 13 to measure the signals with a predetermined frequency based on the clock signals provided by the oscillator 116. Additionally, the signal processing unit 111 can obtain the pulse transit time (PTT) from the ECG signals and PPG signals based on the clock signals to calculate the blood pressure.

The power convertor 117, such as a bulk DC-DC convertor, can convert an input direct-current voltage into another direct-current voltage less than the input direct-current voltage and provide the converted direct-current voltage to the circuit. For example, the power converter 117 can provide corresponding voltages to each of the sensor units, the signal processing unit or the control chips, such as the gravity sensor 115, the photo sensing control chip 130 and ECG sensing control chip 121.

Figure 3C:
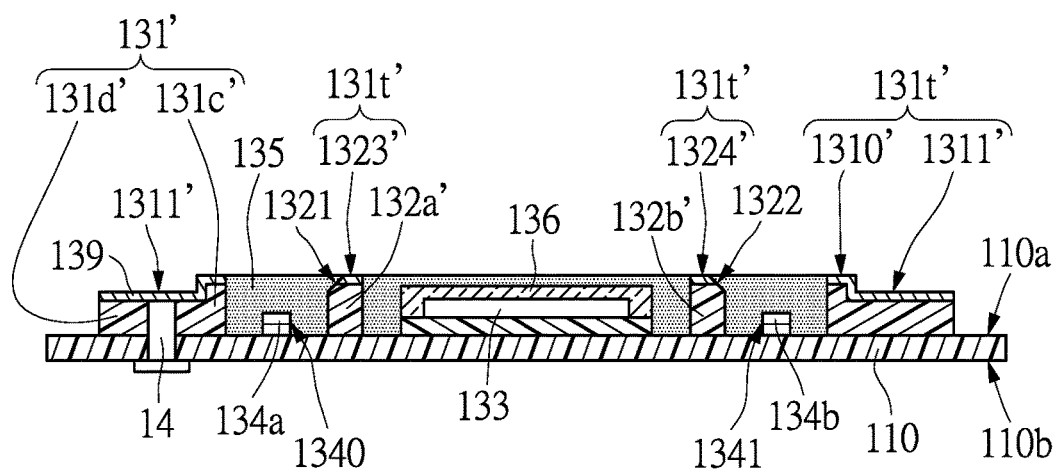
FIG. 3C shows a cross-sectional view of a physiological information measurement module according to a second embodiment of the instant disclosure.

Please refer to FIG. 3C. FIG. 3C shows a cross-sectional view of a physiological information measurement module according to a second embodiment of the instant disclosure. The same reference numerals are given to the same components or to components corresponding to those in FIG. 3B, and descriptions of the common portions are omitted.

A difference between this embodiment and the previous embodiment is that the grid 131' of this embodiment is not completely made of conductive material. That is to say, only a portion of the grid 131' is made of conductive material, and the other portions are made of insulating material. Specifically, the grid 131' of the instant embodiment further includes a conductive layer 139, and the inner conductive contact portion 131e is the surface of the conductive layer 139 exposed from the wearable holder 10.

Accordingly, the top portions of first partition portion 132a' and the second partition portion 132b' commonly form a portion of the conductive layer 139. The inner conductive contact portion 131e includes the top surface 1311' of the outer surrounding portion 131d', the top surface 1310' of the inner surrounding portion 131c', the top surface 1323' of the first partition portion 132a', and the top surface 1324' of the second partition portion 132b'.

In addition, in the instant embodiment, the conductive post 14 is positioned at the outer surrounding portion 131d' and passes through the grid 131' and the circuit board 110 to establish the electrical connection between the inner conductive contact portion 131e and the second pad 113, which is electrically connected to the ECG sensing control chip 121.

The conductive layer 139 of the grid 131' is formed at a side away from the circuit board 110. The grid 131' can be fabricated by embedding the metal into the plastic member to save cost and decrease weight.

Figure 3D:
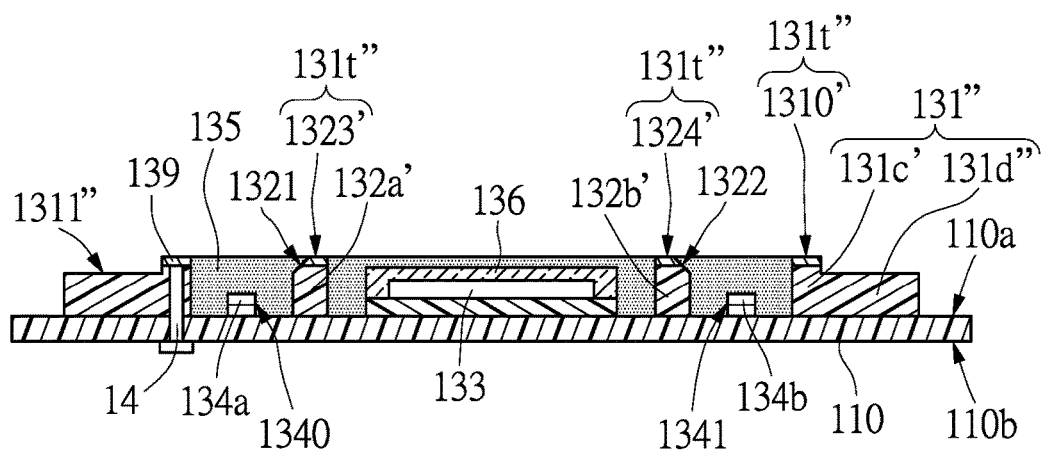
FIG. 3D shows a cross-sectional view of a physiological information measurement module according to a third embodiment of the instant disclosure.

Please refer to FIG. 3D. FIG. 3D shows a cross-sectional view of a physiological information measurement module according to a third embodiment of the instant disclosure similar to the embodiment shown in FIG. 3C, the grid 131" of the instant embodiment includes the conductive layer 139 positioned at the side away from the circuit board 110 so as to form the inner conductive contact portion 131t", and the other portions of the grid 131" are made of insulating material.

A difference between this embodiment and the previous embodiment shown in FIG. 3C is that only the top portions of the inner surrounding portion 131c', the first partition portion 132a', and the second partition portion 132b' have the conductive layer 139, and the outer surrounding portion 131d" is insulated.

Accordingly, in the instant embodiment, the top surface 1311" is not a part of the inner conductive contact portion 131t". That is, the top surface 1310' of the inner surrounding portion 131c', the top surface 1323' of the first partition portion 132a', and the top surface 1324' of the second partition portion 132b' are mated to form the inner conductive contact portion 131t".

Additionally, the conductive post 14 of the instant embodiment is arranged in the inner surrounding portion 131c' corresponding to the position of the inner conductive contact portion 131t". The conductive post 14 passes through the inner surrounding portion 131c' and the circuit board 110 so that the conductive layer 139 can be electrically connected to the ECG sensing control chip 121 located on the rear surface 110b of the circuit board 110.

As long as the inner conductive contact portions 131t, 131f, 131t" adapted to be touched by the user' skin are made of conductive material and electrically connected to the ECG sensing control chip 121, the materials of the grid 131, 131',131" are not limited. The grid can be partially made of insulator and partially made of conductive material to save cost and lighten the weight.

Figure 4A:
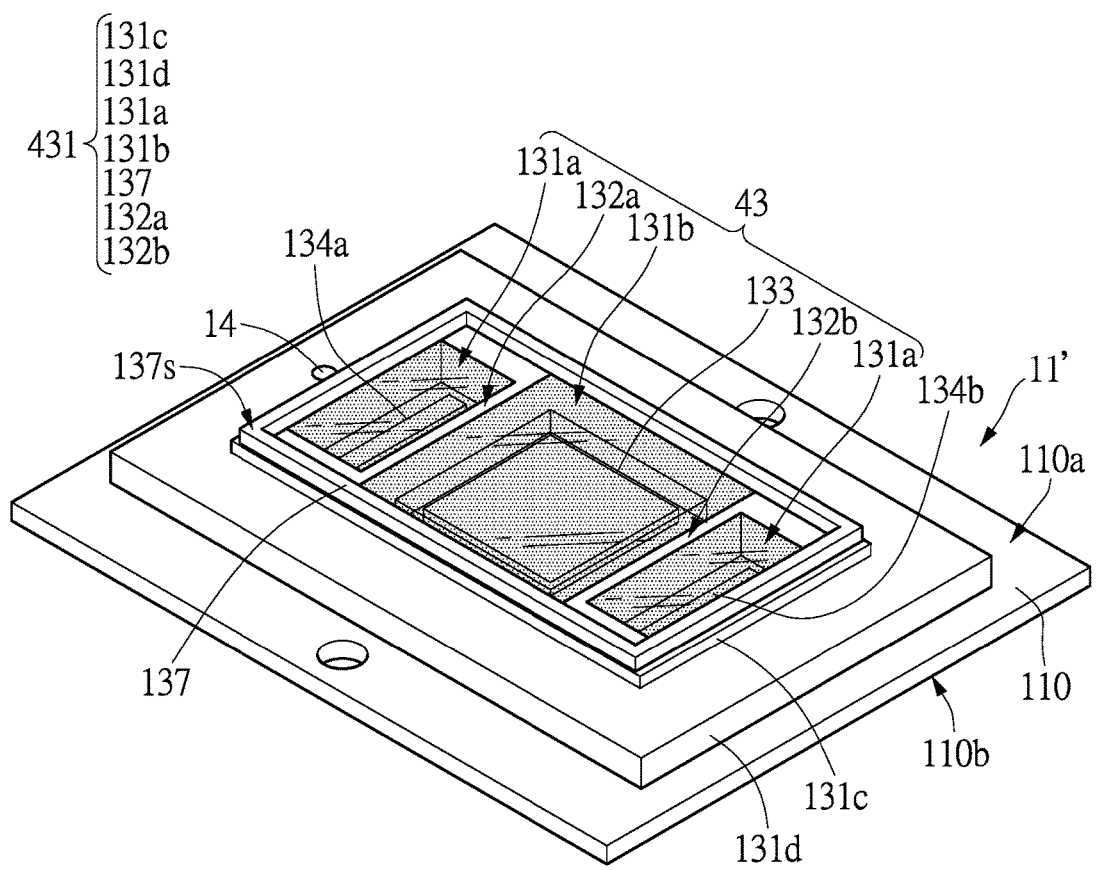
FIG. 4A shows a perspective view of the physiological information measurement module according to a fourth embodiment of the instant disclosure.
Figure 4B:
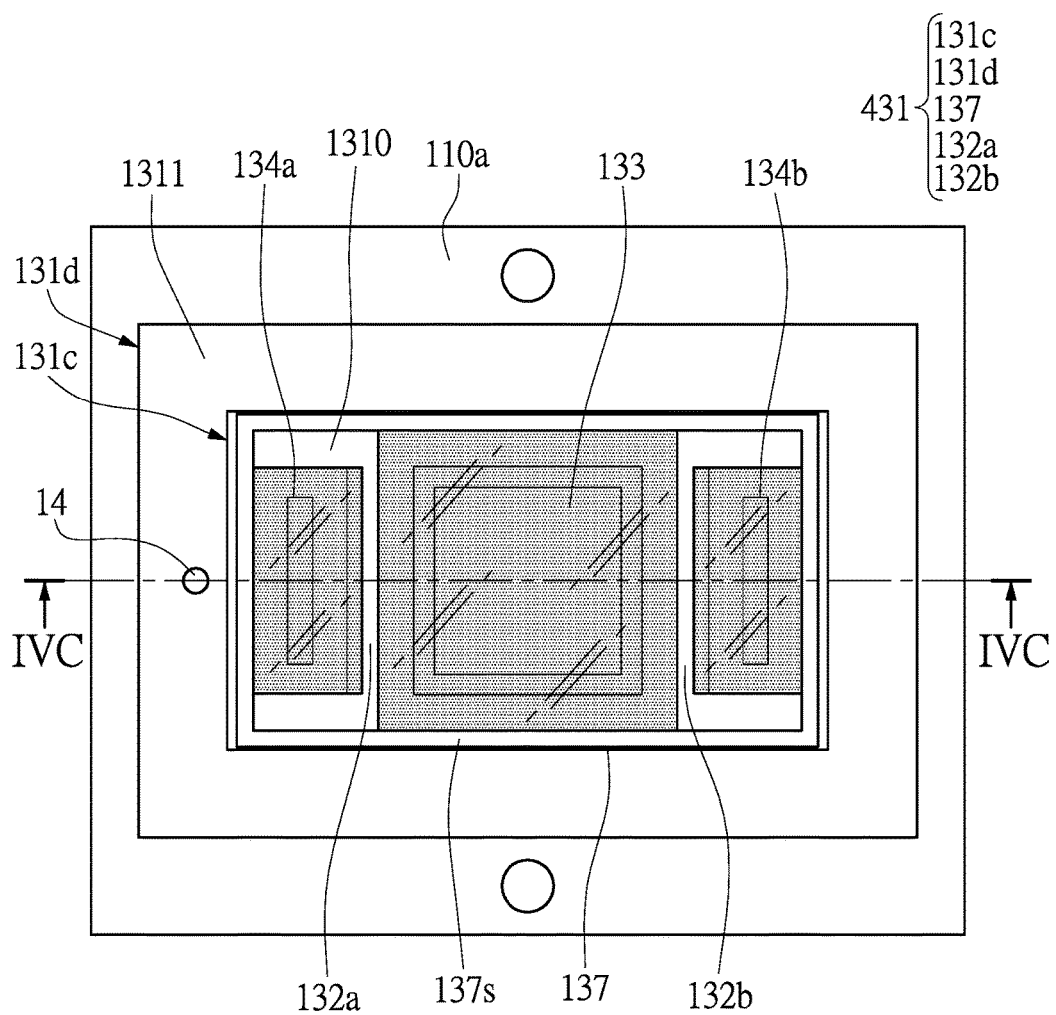
FIG. 4B shows a top view of the physiological information measurement module shown according to the fourth embodiment of the instant disclosure.
Figure 4C:
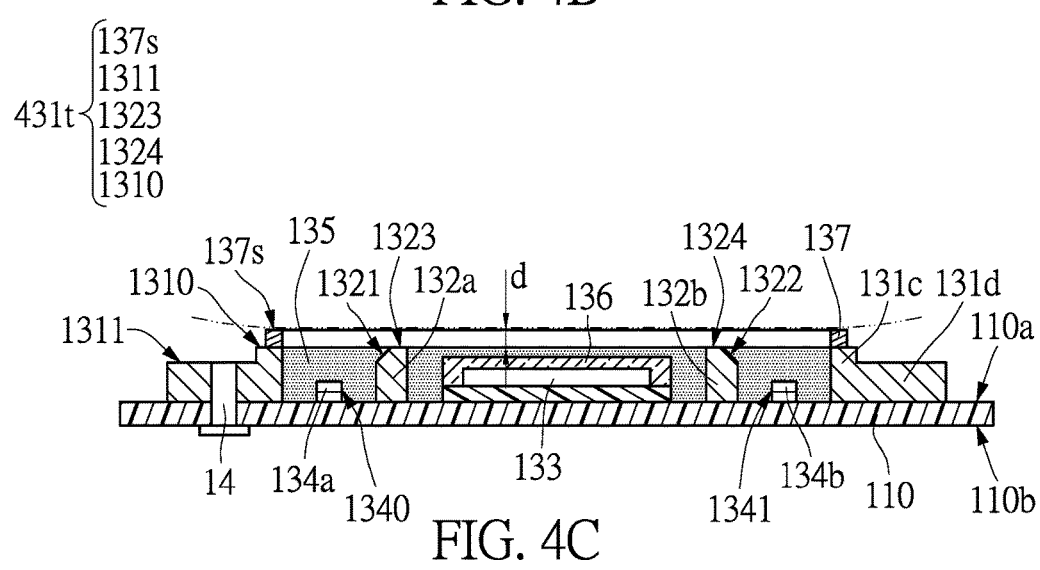
FIG. 4C shows a cross-sectional view taken along line IVC-IVC in FIG. 4B.

Please refer to FIG. 4A, FIG. 4B and FIG. 4C. FIG. 4A shows a perspective view of the physiological information measurement module according to a fourth embodiment of the instant disclosure; FIG. 4B shows a top view of the physiological information measurement module shown according to the fourth embodiment of the instant disclosure; and FIG. 4C shows a cross-sectional view taken along line IVC-IVC in FIG. 4B.

The same reference numerals are given to the same components or to components corresponding to those in FIG. 2A, and descriptions of the common portions are omitted.

As shown in FIG. 4A and FIG. 4B, a difference between the physiological information measurement module 11' of this embodiment and the previous embodiment shown in FIG. 2A is that the grid 431 of the PPG sensor unit 43 further includes a surrounding conductive frame 137 additionally disposed on the inner surrounding portion 131c. Furthermore, the surrounding conductive frame 137 surrounds the first lighting element 134a, the second lighting element 134b, and the photo sensor 133.

Please refer to FIG. 4C. The surrounding conductive frame 137 protrudes from a top surface of the protection layer 135. In one embodiment, the thickness of the surrounding conductive frame 137, i.e., a vertical height d between the top surface of the surrounding conductive frame 137 and the top surface of the protection layer 135, ranges from 0.1 mm to 2 mm.

When the user's wrist (the imaginary line shown in FIG. 4C) is in contact with the surrounding conductive frame 137, the surrounding conductive frame 137 abuts the user's wrist to isolate the ambient light from entering the photo sensor 133 and reduce the interference from the ambient light, thereby improving the accuracy of the detected PPG signals.

In addition, the surrounding conductive frame 137 is disposed on the inner surrounding portion 131c. In the instant embodiment, the inner surrounding portion 131c and the outer surrounding portion 131d are made of conductive materials, and the surrounding conductive frame 137 is electrically connected to the ECG sensing control chip 121 through the inner surrounding portion 131c, the outer surrounding portion 131d and the conductive post 14, in which the conductive post passes through the circuit board 110 and the outer surrounding portion 131d. The ECG signals can be measured by the user respectively touching the top surface 137s of the surrounding conductive frame 137 and the outer conductive contact portion 120 with the user's two hands.

However, the surrounding conductive frame 137 of the instant embodiment partially covers the top surface 1310 of the inner surrounding portion 131c, and hence the inner conductive contact portion 431t can include the top surface 137s of the surrounding conductive frame 137, the top surface 1323 of the first partition portion 132a, the top surface 1324 of the second conductive portion 132b, a portion of the top surface 1310 of the inner surrounding portion 131c and the top surface 1311 of the outer surrounding portion 131d. Although FIG. 4C illustrates that the user's wrist only touches the top surface 137s of the surrounding conductive frame 137, in practice, the user can touch any position of the inner conductive contact portion 431t.

Figure 5A:
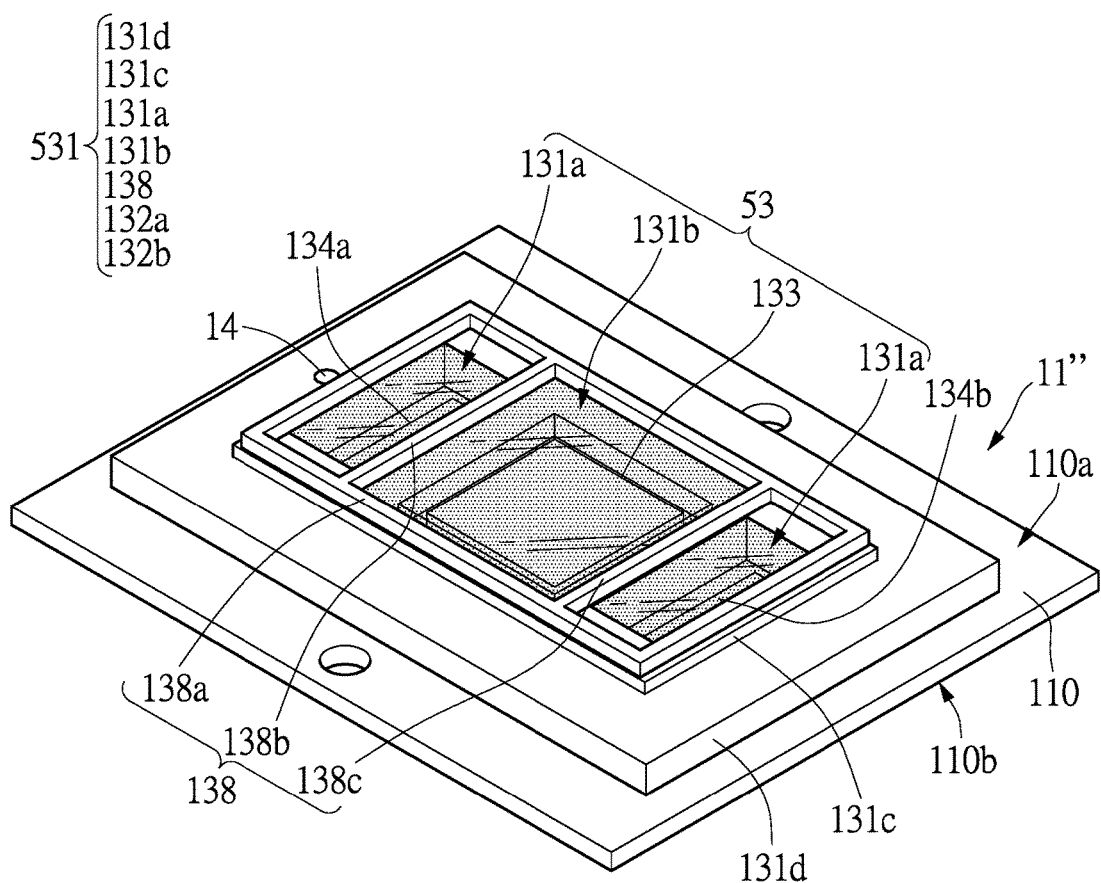
FIG. 5A shows a perspective view of the physiological information measurement module according to a fifth embodiment of the instant disclosure.
Figure 5B:
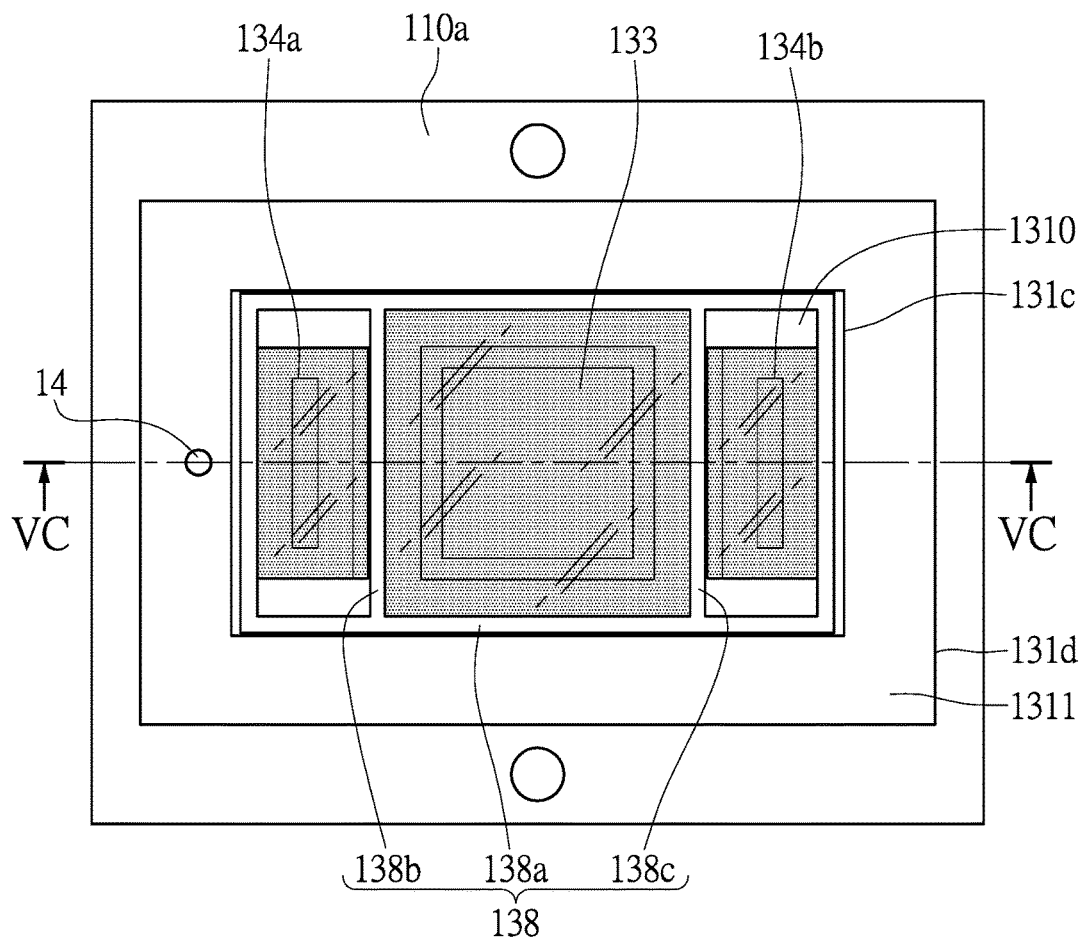
FIG. 5B shows a top view of the physiological information measurement module shown according to the fifth embodiment of the instant disclosure.
Figure 5C:
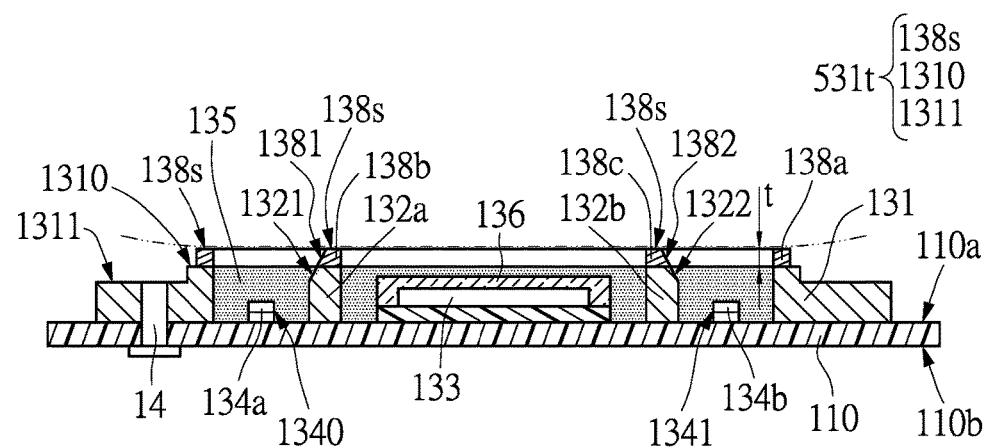
FIG. 5C shows a cross-sectional view taken along line VC-VC in FIG. 5B.

Please refer to FIG. 5A to FIG. 5C. FIG. 5A shows a perspective view of the physiological information measurement module according to a fifth embodiment of the instant disclosure; FIG. 5B shows a top view of the physiological information measurement module shown according to the fifth embodiment of the instant disclosure; and FIG. 5C shows a cross-sectional view taken along line VC-VC in FIG. 5B.

The same descriptions of the instant embodiment as the other embodiment shown in FIG. 4A are omitted herein. As shown in FIG. 5A and FIG. 5B, in the physiological information measurement module 11" of the instant embodiment, the grid 531 of the PPG sensor unit 53 includes the other type of the surrounding conductive frame 138.

The surrounding conductive frame 138 of the instant embodiment includes an outer frame 138a and a plurality of frame strips 138b, 138c. The outer frame 138a is disposed on the inner surrounding portion 131c, and the frame strips 138b, 138c are respectively disposed on the first partition portion 132a and the second partition portion 132b. In other words, the surrounding conductive frame 138 of the instant embodiment has a grid structure similar and corresponding to the grid 131.

As shown in FIG. 5C, all of the outer frame 138a and the frame strips 138b, 138c protrude from the top surface of the protection layer 135. Furthermore, the top portion of the frame strip 138b has the inclined surface 1381 extending from the first inclined light-guiding surface 1321, and the portion of the frame strip 138c has the inclined surfaces 1382 extending from the second inclined light-guiding surface 1322. As such, the detecting lights produced by the first lighting element 134a and the second lighting element 134b can be guided onto the object to be tested.

Specifically, the inclined surface 1381 of the frame strip 138b and the first inclined light-guiding surface 1321 are parallel to each other and form a continuous plane. That is, the extending direction of the inclined surface 1381 of the frame strip 138b also can pass through the side surface 1340 of the first lighting element 134a. Similarly, the inclined surface 1382 of the frame strip 138c and the second inclined light-guiding surface 1322 are parallel to each other and form a continuous plane. Preferably, the extending direction of the inclined surface 1382 of the frame strip 138c also can pass through the side surface 1341 of the second lighting element 134b. Accordingly, similar to the embodiment shown in FIG. 3B, the inclined surfaces 1381, 1382 are inclined with the front surface 110a of the circuit board 110 by an angle ranging from 10 to 80 degrees. In one preferred embodiment, the angle ranges from 25 to 65 degrees due to the size limitation.

When the detecting lights produced by the first lighting element 134a and the second lighting element 134b are monochromatic, the inclined surface 1381 of the frame strip 138b and the inclined surface 1382 of the frame strip 138c are substantially symmetrical with each other and inclined with respect to the horizontal reference plane by substantially the same angle.

Similar to the embodiment shown in FIG. 4C, when the user's wrist (the imaginary line shown in FIG. 5C) is in contact with the surrounding conductive frame 138, the surrounding conductive frame 138 abuts the user's wrist to isolate the ambient light from entering the photo sensor 133 and reduce the interference from the ambient lights, thereby improving the accuracy of the detected PPG signals.

Additionally, in the instant embodiment, the surrounding conductive frame 138 is disposed on the inner surrounding portion 131c and partially covers the top surface 1310 of the inner surrounding portion 131c. Accordingly, the inner conductive contact portion 531t of the instant embodiment includes the top surface 138s of the surrounding conductive frame 138, a portion of the top surface 1310 of the inner surrounding portion 131c, and the top surface 1311 of the outer surrounding portion 131d. Although FIG. 5C illustrates that the user's wrist only touches the top surface 138s of the surrounding conductive frame 138, in practice, the user can touch any position of the inner conductive contact portion 531t.

Notably, in the embodiments respectively shown in FIG. 4C and FIG. 5C, the grids 431, 531 and the surrounding conductive frames 137, 138 can be partially made of conductive material and partially made of insulating material. For example, the grids 431, 531 and the surrounding conductive frames 137, 138 can be fabricated by embedding metal into the plastic member to form the inner conductive contact portions 431t, 531t exposed from the wearable holder 10, thereby saving cost and decreasing weight.

Figure 6:
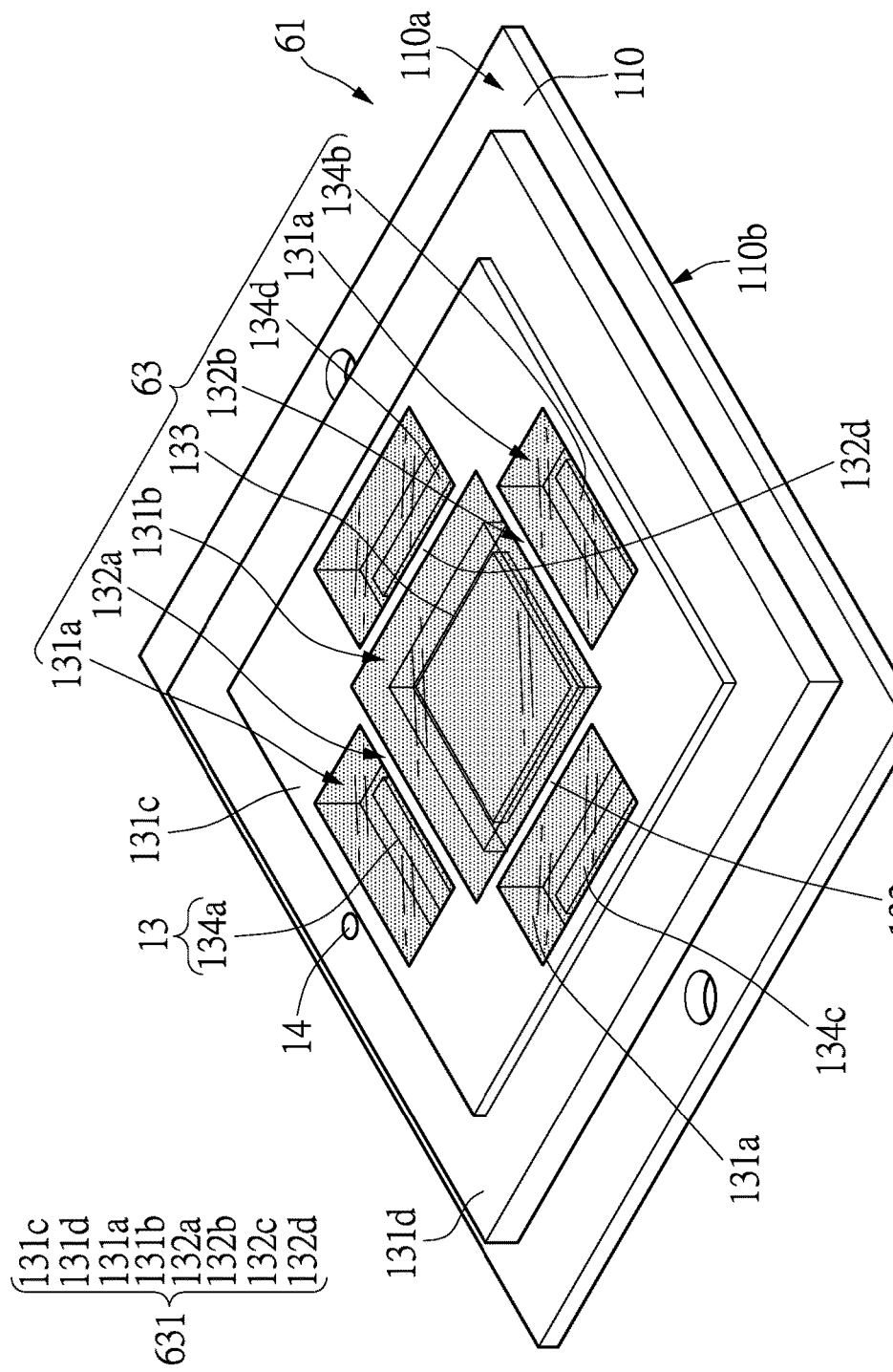
FIG. 6 shows a perspective view of the physiological information measurement module according to another embodiment of the instant disclosure.

Please refer to FIG. 6. FIG. 6 shows a perspective view of the physiological information measurement module according to another embodiment of the instant disclosure. The same reference numerals are given to the same components or to components corresponding to those in FIG. 2A.

In the instant embodiment, the PPG sensor unit 63 of the physiological information measurement module 61 includes a plurality of lighting elements surrounding the photo sensor 133. As shown in FIG. 6A, the first lighting element 134a, the second lighting element 134b, the third lighting element 134c, and the fourth lighting element 134d surround the photo sensor 133 to project the detecting lights. Specifically, the third lighting element 134c and the fourth lighting element 134d are respectively arranged at two opposite sides of the photo sensor 133.

The wavelengths of the detecting lights produced by the first, second, third and fourth lighting element 134a-134d are not necessarily the same. That is, the first, second, third and fourth lighting element 134a-134d can produce the detecting lights with different wavelengths according to practical demands.

In addition, due to the arrangements of the third and fourth lighting elements 134c, 134d, the grid 631 further includes a third partition portion 132c disposed between the third lighting element 134c and the photo sensor 133 and a fourth partition portion 132d disposed between the fourth lighting element 134d and the photo sensor 133.

Similar to the first partition portion 132a and the second partition portion 132b, the top portion of the third partition portion 132c has a third inclined light-guiding surface (not shown), and the top portion of the fourth partition portion 132d has a fourth inclined light-guiding surface (not shown). The third and fourth inclined light-guiding surfaces are inclined 10 to 80 degrees with respect to the front surface 110a of the circuit board 110. In one preferred embodiment, the third and fourth inclined light-guiding surfaces are inclined 25 to 65 degrees with respect to the front surface 110a of the circuit board 110. Furthermore, the inclined angle of the third inclined light-guiding surface with respect to the circuit board 110 is not necessarily the same as that of the first inclined light-guiding surface.

In one embodiment, an extending direction of the third inclined light-guiding surface passes through a side surface of the third lighting element 134c which faces to the third partition portion 132c. Similarly, an extending direction of the fourth inclined light-guiding surface passes through a side surface of the forth lighting element 134d which faces to the fourth partition portion 132d.

Figure 7:
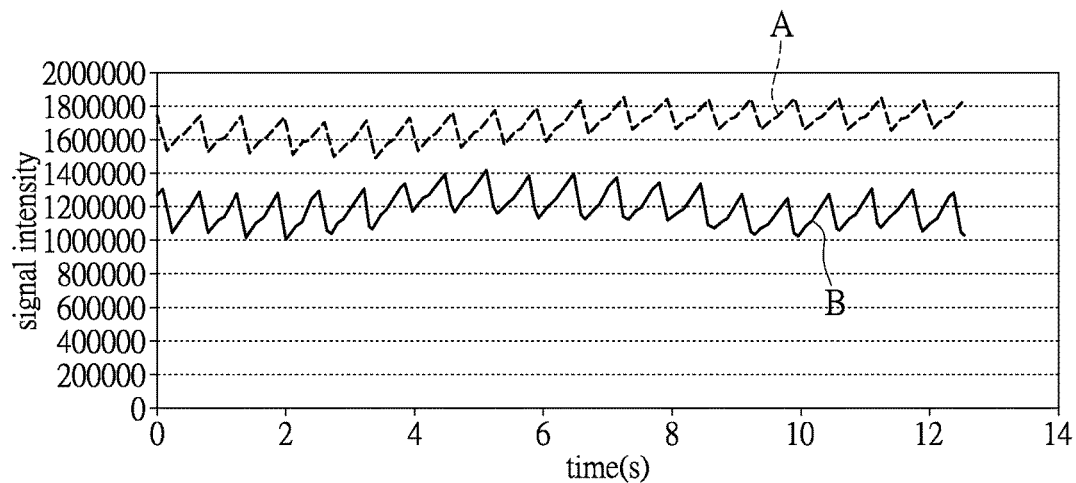
FIG. 7 shows the PPG signals measured under the conditions that the surrounding conductive frames have different thicknesses.

Please refer to FIG. 7. FIG. 7 shows the PPG signals measured under the conditions that the surrounding conductive frames have different thicknesses. Take the embodiment shown in FIG. 5 as an example. The thickness of the surrounding conductive frame 138 means the vertical height t between the top surface 138s of the surrounding conductive frame 138 and top surface of the protection layer 135.

The curve A shown in FIG. 7 presents the PPG signals measured at different time points under the condition that the thickness of the surrounding conductive frame 138 is 0.1 mm, and the curve B presents the PPG signals measured at different time points under the condition that the thickness of the surrounding conductive frame 138 is 0.51 mm.

As shown in FIG. 7, the difference between the maximum value and the minimum value of the curve B is greater than that of the curve A. That is, the thicker the surrounding conductive frame 138 is, the larger the difference between the maximum value and the minimum value of the measured PPG signals. Accordingly, FIG. 7 illustrates that the thicker surrounding conductive frame 138 is helpful to improve the sensitivity of the measured PPG signals.

Figure 8:
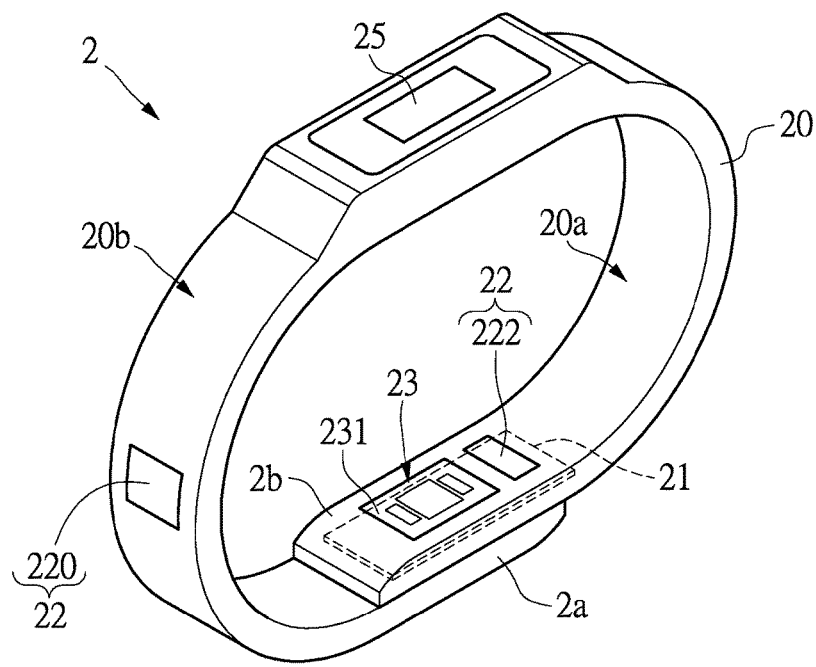
FIG. 8 shows a perspective view of a wearable blood-pressure measuring apparatus according to anther embodiment of the instant disclosure.

Please refer to FIG. 8. FIG. 8 shows a perspective view of a wearable apparatus according to anther embodiment of the instant disclosure. Similar to the wearable apparatus 1 shown in FIG. 1, the wearable apparatus 2 includes a wearable holder 20 and a physiological information measurement module 21 arranged in the wearable holder 20. In the instant embodiment, the wearable holder 20 has two opposite ending portions 2a, 2b. Furthermore, the wearable holder 20 includes a male fastener and a female fastener for mating with the male fastener respectively disposed at two opposite ending portions 2a, 2b. In the instant embodiment, the physiological information measurement module 21 is configured at the ending portion 2b.

In addition, the wearable apparatus 2 can further include a display module 25 configured on the wearable holder 20 and between two opposite ending portions 2a, 2b for displaying the blood pressure measured by the physiological information measurement module 21.

Similar to the physiological information measurement module 11, the physiological information measurement module 21 of the instant embodiment includes a circuit board (not shown), an ECG sensor unit 22, and a PPG sensor unit 23. The circuit board of the physiological information measurement module 21 can be similar to the circuit board 110 of the physiological information measurement module 11 shown in FIG. 2A or FIG. 2B, and the relative descriptions are omitted.

In the instant embodiment, the outer conductive contact portion 220 of the ECG sensor unit 22 is arranged between the display module 25 and the ending portion 2a and exposed on the outer surface 20b of the wearable holder 20 to be touched by the user. The outer conductive contact portion 220 can be electrically connected to the ECG sensing control chip (not shown in FIG. 7, and refer to FIG. 2B) on the circuit board (not shown in FIG. 7, and refer to FIG. 2B) through the traces (not shown) configured in the wearable holder 20. Additionally, the ECG sensor unit 22 also includes a ground electrode 222 to attenuate the noise introduced into the ECG signals.

The grid 231 of the PPG sensor unit 23 is exposed at the inner surface 20a of the wearable holder 20 to be touched by the user and serve as one of the signal input electrodes of the ECG sensor unit 22. The person may have whiter skin at the inside of the wrist than that at the outside of the wrist, thus, it is more easy for the PPG sensor unit 23 arranged at the ending portion 2b of the wearable holder 20 to obtain better PPG signals.

In summary, in the wearable apparatus and the PPG sensor unit provided in the instant disclosure, the grid of the PPG sensor unit can serve as one of the signal input electrodes of the ECG sensor unit so that the space occupation of the PPG sensor unit and ECG sensor unit can be minimized effectively, thereby minimizing and decreasing the size and weight of the wearable apparatus.

Furthermore, in one embodiment of the instant disclosure, the surrounding conductive frame is disposed on the grid to serve as a portion of the inner conductive contact portion to be easily touched by the user and measure the ECG signal. Additionally, the surrounding conductive frame surrounding the photo sensor and the lighting elements can prevent the ambient light from entering the photo sensor, thereby improving the accuracy of the PPG signals.

The descriptions illustrated supra set forth simply the preferred embodiments of the instant disclosure; however, the characteristics of the instant disclosure are by no means restricted thereto. All changes, alterations, or modifications conveniently considered by those skilled in the art are deemed to be encompassed within the scope of the instant disclosure delineated by the following claims.

What is claimed is:

1. A photoplethysmograph sensor unit adapted to be disposed in a wearable holder for use in conjunction with an electrocardiography sensor unit, comprising:
   a circuit board having a pad disposed thereon;
   a grid disposed on the circuit board and defining a plurality of accommodating spaces, wherein the grid includes an inner conductive contact portion electrically connected to the pad on the circuit board, and the inner conductive contact portion is exposed from an inner surface of the wearable holder;
   a first lighting element arranged in one of the accommodating spaces; and
   a photo sensor arranged in another accommodating space;

wherein the inner conductive contact portion surrounds an area occupied by the first lighting element and the photo sensor in a continuous manner.

2. The photoplethysmograph sensor unit according to claim 1, wherein the inner conductive contact portion is electrically connected to the electrocardiography sensor unit through a conductive post passing through the grid and the circuit board.

3. The photoplethysmograph sensor unit according to claim 1, wherein the grid includes a conductive layer positioned at a side of the grid away from the circuit board or a surrounding frame surrounding the first lighting emitting element and the photo sensor, and a top surface of the conductive layer or a top surface of the surrounding frame is a part of the inner conductive contact portion.

4. The photoplethysmograph sensor unit according to claim 3, wherein the grid comprises a first partition portion arranged between the first lighting element and the photo sensor, and the first partition portion comprises a first inclined light-guiding surface formed at a top portion thereof and adjacent to the first lighting element.

5. The photoplethysmograph sensor unit according to claim 4, further comprising a second lighting element arranged in another accommodating space, wherein the grid has a second partition portion arranged between the second lighting element and the photo sensor, the second partition portion has a second inclined light-guiding surface formed at a top portion thereof and adjacent to the second lighting element.

6. The photoplethysmograph sensor unit according to claim 5, wherein the first inclined light-guiding surface formed is inclined along a direction from a top surface of the first partition portion to the first lighting element, the second inclined light-guiding surface is inclined along a direction from a top surface of the second partition portion to the second lighting element, and the first and second inclined light-guiding surfaces are inclined with respect to the circuit board by an angle ranging from 10 to 80 degrees.

7. The photoplethysmograph sensor unit according to claim 1, wherein the grid further comprises a first partition portion arranged between the first lighting element and the photo sensor, the first partition portion has a first inclined light-guiding surface formed at a top portion thereof, and adjacent to the first lighting element, the first inclined light-guiding surface is inclined along a direction from a top surface of the first partition portion to the first lighting element, and the first inclined light-guiding surface is inclined with respect to the circuit board by an angle ranging from 10 to 80 degrees.

8. The photoplethysmograph sensor unit according to claim 1, wherein the grid includes a first partition portion arranged between the first lighting element and the photo sensor, the first partition portion includes a first inclined light-guiding surface formed at a top portion thereof and adjacent to the first lighting element, the first lighting element has a side surface arranged facing to the first partition portion, and an extending direction of the first inclined light-guiding surface passes through the side surface of the first lighting element.

9. The photoplethysmograph sensor unit according to claim 1, wherein the inner conductive contact portion comprises a rough contact surface on which a surface treatment has been performed so as to increase the contacting area.

10. The photoplethysmograph sensor unit according to claim 1, further comprising a filter layer disposed on the photo sensor and a protection layer covering the first lighting element and the photo sensor.

11. A wearable apparatus for sensing blood-pressure of a user, the wearable apparatus comprising:
a wearable holder having an inner surface and an outer surface; and
a physiological information measurement module arranged within the wearable holder and comprising:
a circuit board including a first pad and a second pad disposed thereon;
an electrocardiography sensor unit having an electrocardiography sensing control chip and an outer conductive contact portion electrically connected to the first pad and exposed at the outer surface of the wearable holder so as to serve as a first signal input electrode of the electrocardiography sensor unit, wherein the electrocardiography sensing control chip is electrically connected to the first pad and the second pad; and
a photoplethysmograph sensor unit, including:
a grid defining a plurality of accommodating spaces and including an inner conductive contact portion electrically connected to the second pad, wherein the inner conductive contact portion of the grid is exposed from the inner surface of the wearable holder to be touched by the user, and thereby serving as a second signal input electrode of the electrocardiography sensor unit;
a first lighting element arranged in one of the accommodating spaces; and
a photo sensor arranged in another accommodating space;
wherein the inner conductive contact portion surrounds an area occupied by the first lighting element and the photo sensor in a continuous manner.

12. The wearable apparatus according to claim 11, wherein the inner conductive contact portion is electrically connected to the electrocardiography sensor unit through a conductive post passing through the grid and the circuit board.

13. The wearable apparatus according to claim 11, wherein the grid includes a conductive layer positioned at a side of the grid away from the circuit board or a surrounding frame surrounding the first lighting emitting element and the photo sensor, and a top surface of the conductive layer or a top surface of the surrounding frame is a part of the inner conductive contact portion.

14. The wearable apparatus according to claim 13, wherein the grid comprises a first partition portion arranged between the first lighting element and the photo sensor, and the first partition portion includes a first inclined light-guiding surface formed at a top portion thereof and adjacent to the first lighting element.

15. The wearable apparatus according to claim 14, further comprising a second lighting element arranged in another accommodating space, wherein the grid has a second partition portion arranged between the second lighting element and the photo sensor, the second partition portion has a second inclined light-guiding surface formed at a top portion thereof and adjacent to the second lighting element.

16. The wearable apparatus according to claim 15, wherein the first inclined light-guiding surface is inclined along a direction from a top surface of the first partition portion to the first lighting element, the second inclined light-guiding surface is inclined along a direction from a top surface of the second partition portion to the second lighting element, and the first and second inclined light-guiding surfaces are inclined with respect to the circuit board by an angle ranging from 10 to 80 degrees.

17. The wearable apparatus according to claim 11, wherein the grid further comprises a first partition portion arranged between the first lighting element and the photo sensor, the first partition portion comprises a first inclined light-guiding surface formed at a top portion thereof, adjacent to the first lighting element, and inclined along a direction from a top surface of the first partition portion to the first lighting element, the first lighting element has a side surface arranged facing to the first partition portion, and an extending direction of the first inclined light-guiding surface passes through the side surface of the first lighting element.

18. The wearable apparatus according to claim 11, wherein the wearable holder comprises two opposite ending portions, and the physiological information measurement module is arranged at one of the ending portions.

19. The wearable apparatus according to claim 18, wherein the wearable holder comprises a male fastener and a female fastener for mating with the male fastener, the male fastener and the female fastener are respectively disposed on two opposite ending portions.

20. The wearable apparatus according to claim 19, further comprising a display module arranged on the wearable holder and positioned between two opposite ending portions.

21. A physiological information measurement module arranged within a wearable holder and comprising:
   a circuit board including a first pad and a second pad disposed thereon;
   an electrocardiography sensor unit having an electrocardiography sensing control chip and an outer conductive contact portion electrically connected to the first pad and exposed at an outer surface of the wearable holder so as to serve as a first signal input electrode of the electrocardiography sensor unit, wherein the electrocardiography sensing control chip is electrically connected to the first pad and the second pad; and
   a photoplethysmograph sensor unit including:
      a grid disposed on the circuit board and defining a plurality of accommodating spaces, wherein the grid includes an inner conductive contact portion electrically connected to the second pad, and the inner conductive contact portion of the grid is exposed from the inner surface of the wearable holder with the inner conductive contact portion facing an inner side of the wearable holder, and thereby serving as a second signal input electrode of the electrocardiography sensor unit;
      a first lighting element arranged in one of the accommodating spaces; and
      a photo sensor arranged in another accommodating space;
      wherein the inner conductive contact portion surrounds an area occupied by the first lighting element and the photo sensor in a continuous manner.

* * * * *